United States Patent [19]

Baum

[11] 4,402,689

[45] Sep. 6, 1983

[54] SANITARY NAPKIN WITH DISPOSAL MEANS

[75] Inventor: Pamela F. Baum, Neenah, Wis.

[73] Assignee: Kimberly-Clark Corporation, Neenah, Wis.

[21] Appl. No.: 284,678

[22] Filed: Jul. 20, 1981

[51] Int. Cl.³ .............................................. A61F 13/16
[52] U.S. Cl. .................................................... 604/387
[58] Field of Search .................. 128/286, 287, 290 R, 128/290 W, 290 P; 604/358, 378, 381, 385, 386–387, 389

[56] References Cited

U.S. PATENT DOCUMENTS

| 3,230,956 | 1/1966 | Kargul | 128/290 R |
| 3,367,334 | 2/1968 | Testa | 128/290 R |
| 3,920,019 | 11/1975 | Schaar | 128/287 |
| 4,015,604 | 4/1977 | Csillag | 128/290 R |
| 4,023,571 | 5/1977 | Comerford et al. | 128/290 R |

*Primary Examiner*—C. Fred Rosenbaum
*Attorney, Agent, or Firm*—Howard Olevsky; Gregory E. Croft; R. Jonathan Peters

[57] ABSTRACT

A sanitary napkin is provided with a baffle approximately twice the width of the conventional baffle. The baffle is folded over onto itself with the garment facing side having a garment suspension adhesive pattern. After the napkin has been used the folded portion is unfolded and placed over the top of the napkin where it is adhesively attached by the garment suspension adhesive pattern placed on the garment facing side of the folded portion of the baffle.

3 Claims, 4 Drawing Figures

SANITARY NAPKIN WITH DISPOSAL MEANS

FIELD OF THE INVENTION

The subject invention relates to a sanitary napkin and particularly to a sanitary napkin with disposal means incorporated therewith.

BACKGROUND OF THE INVENTION

One of the problems associated with the use of sanitary napkins has been their disposal. Used napkins are unattractive and can be messy. Attempts to provide disposal aids have generally followed one of two directions. The first of these involves the use of a bag or bag-like attachment affixed to or as part of a sanitary napkin. Examples of various embodiments of this approach can be found in U.S. Pat. No. 4,182,336; 3,604,423 and 3,274,999.

The self-contained bag has been unsuccessful for a variety of reasons. The self-contained bag is on the bottom of the napkin and therefore must, by its nature, interfere with adhesive attachment of the napkin to the panty. Also, a napkin with such a self-contained bag is both expensive and difficult to manufacture.

Another alternative involves the utilization of adhesive areas at the longitudinal ends of the garment facing side of the napkin. These adhesive areas may be covered by an extension or an added element and after the napkin is used, it is rolled into a tightly wound cylinder with the adhesive tab being used to fasten the roll. This approach, while simpler from a manufacturing standpoint, still involves the use of a separate tab and the user of the napkin must touch the soiled napkin to be able to roll it. Also, extremely thick napkins are difficult to roll because of limited flexibility. The pressure involved in rolling a napkin can, in certain instances provide for fluid "strikeback" through the wrapper of the napkin. For this reason a disposal system of the type disclosed in U.S. Pat. No. 3,626,945 has met with little success.

U.S. Pat. Nos. 2,742,903 and 4,072,151 have a structure which places adhesive on the body-facing side of the sanitary napkin for direct attachment to the wearer.

SUMMARY OF THE INVENTION

According to this invention a sanitary napkin having an absorbent layer wrapped with a fluid permeable wrap is provided with a baffle approximately twice the width of the conventional baffle. The baffle is attached to the bottom of the outside portion of the wrap so that the baffle is fully exposed. The baffle is also folded over onto itself. The fold is maintained in place by positioning means such as an adhesive area and the garment facing side of the folded baffle is provided with garment suspension adhesive or other attachment means. After the napkin is used the baffle is unfolded with the free flap positioned over the top portion of the napkin and attached by adhesive or other means to either the wrap or the opposite side of the baffle. The used portion of the napkin is at least partially visually screened and the napkin can be readily disposed of without the user having to touch the soiled napkin surface.

BRIEF DESCRIPTION OF THE DRAWINGS

This invention may more readily be understood by reference to the drawings in which.

Figure 1:
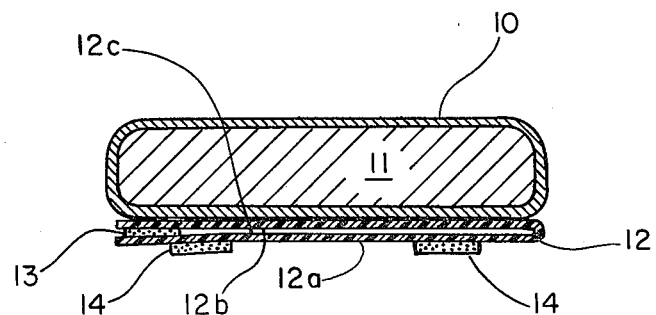
FIGS. 1 and 3 are cross sections of alternative embodiments of the subject invention and FIGS. 2 and 4 are cross sections of the embodiments of FIGS. 1 and 3 respectively showing the napkin with the baffle in place after use. In each instance like numbers relate to like components.
Figure 2:
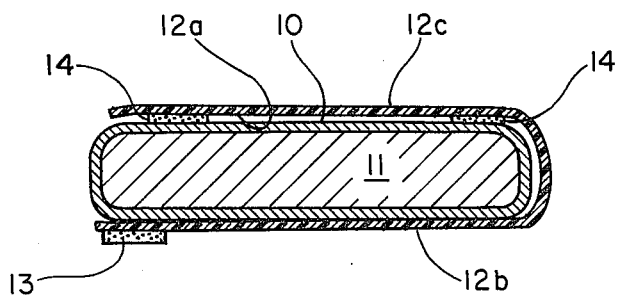

According to FIG. 1 a sanitary napkin having an absorbent layer 11 is encircled with a fluid permeable layer 10. Attached to the bottom of the fluid permeable 10 is baffle 12. Unlike some napkin constructions, the baffle is attached to the outside of the fluid permeable wrap. As can be seen from FIG. 1 the baffle is approximately twice the width of conventional baffles and has a bottom folded side 12a, a top folded side 12c and an inner surface 12b. The fold is maintained and the baffle attached to itself by positioning means such as adhesive 13. The napkin as illustrated in this figure is attached to the undergarments by suspension adhesive 14.

After use, the baffle is unfolded and the garment facing side 12a is placed over the top portion of the used napkin and maintained there by compression on the pressure sensitive adhesive 14. The inner facing side 12c becomes the topmost surface of the napkin.

Figure 3:
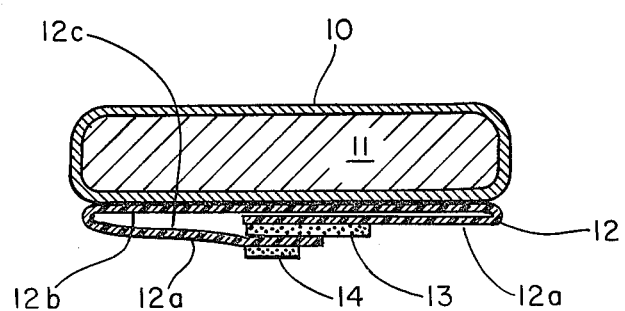
Figure 4:
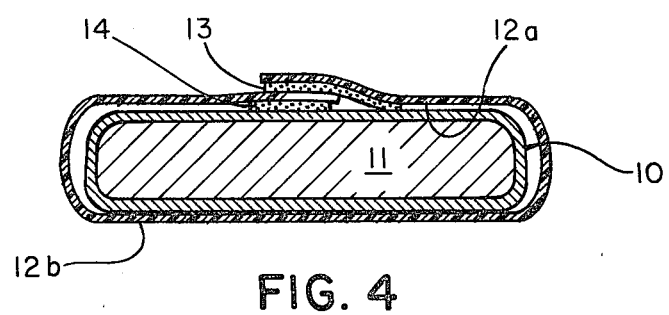

The second embodiment of this invention is shown at FIG. 3 in which there are substantially equal projections of the baffle to form bottom facing sides 12a extending from each side of the napkin. According to this particular configuration a wider adhesive strip 13 is used both to maintain the napkin in its folded configuration at its outer edges and also to provide a portion of the garment suspension adhesive along with adhesive area 14. As can be seen in FIG. 4, the edges are unfolded after use with the adhesive area 14 used to adhere one side of the inward facing side 12 to the top of the napkin while the combined adhesive area 13 attaches the other portion of the baffle fold to either the first folded baffle portion and the exposed portion of the top of the napkin. (It is apparent that the adhesive can be used to attach to either the first folded baffle portion or to the wrap within the spirit of this invention.)

While it should be noted that the attachment means for the wrap to the baffle are not shown, attachment of these components is conventional and any of the means known in the art can be used such as adhesive attachment or fusing or combinations thereof.

It is also possible to lightly fuse the baffle to itself such as by ultrasonic means to eliminate the inner adhesive 13. While other modifications will readily suggest themselves to those with reasonable skill in the art, the concept of the subject invention, broadly stated, is the application of a baffle of extended width to cover the body facing side of the sanitary napkin to provide a suitable disposal means.

What is claimed is:

1. A sanitary napkin with a body facing surface and a garment facing surface having, in combination, an absorbent layer, a fluid permeable wrap overlying the absorbent layer at least on its body facing surface and a fluid impermeable baffle providing said garment facing surface, said baffle being of sufficient transverse dimension to overwrap said body facing surface, said baffle being folded upon itself with said folds being adhesively secured in place and said baffle also having adhesive attachment means on said garment facing surface for attaching the napkin to a garment.

2. The napkin according to claim 1 wherein the baffle is folded along one longitudinal edge.

3. The napkin according to claim 1 wherein the baffle is folded along each longitudinal edge with each flap formed being substantially equal in transverse direction.

* * * * *